United States Patent [19] 
Leppard et al.

[11] Patent Number: 4,629,682
[45] Date of Patent: Dec. 16, 1986

[54] RECORDING MATERIAL FOR COLOR PHOTOGRAPHY

[75] Inventors: David G. Leppard, Marly; Jean Rody, Riehen, both of Switzerland

[73] Assignee: Ciba-Geigy AG, Basel, Canada

[21] Appl. No.: 717,096

[22] Filed: Mar. 28, 1985

Related U.S. Application Data

[63] Continuation-in-part of Ser. No. 559,433, Dec. 8, 1983, abandoned.

[30] Foreign Application Priority Data

Dec. 8, 1982 [CH] Switzerland .......................... 7142/82

[51] Int. Cl.$^4$ .......................... G03C 1/40; G03C 1/84
[52] U.S. Cl. .................................. 430/372; 430/512; 430/551; 430/559
[58] Field of Search ............... 430/372, 505, 551, 512, 430/559

[56] References Cited

U.S. PATENT DOCUMENTS

| | | | |
|---|---|---|---|
| 4,226,999 | 10/1980 | Malherbe et al. | 546/190 |
| 4,268,593 | 5/1981 | Leppard et al. | 430/17 |
| 4,316,837 | 2/1982 | Molt et al. | 260/45.8 N |
| 4,340,533 | 7/1982 | Rody | 524/99 |
| 4,452,884 | 6/1984 | Leppard | 430/523 |
| 4,465,757 | 8/1984 | Leppard et al. | 430/551 |
| 4,465,765 | 8/1984 | Leppard et al. | 430/551 |
| 4,496,649 | 1/1985 | Leppard et al. | 430/551 |

FOREIGN PATENT DOCUMENTS

| | | |
|---|---|---|
| 0011051 | 5/1980 | European Pat. Off. . |
| 0013443 | 7/1980 | European Pat. Off. . |
| 0047605 | 3/1982 | European Pat. Off. . |

Primary Examiner—Richard L. Schilling
Attorney, Agent, or Firm—Wenderoth, Lind & Ponack

[57] ABSTRACT

Recording material for color photography which contains in at least one photosensitive silver halide emulsion layer, one intermediate layer and/or one protective layer, at least one polyalkylpiperidine compound of the formula I

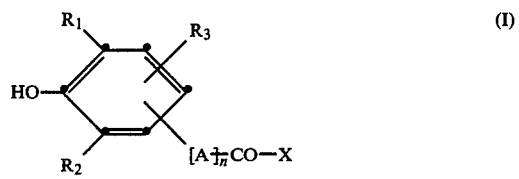

in which n is the number 0 or 1 and X is a group of the formula

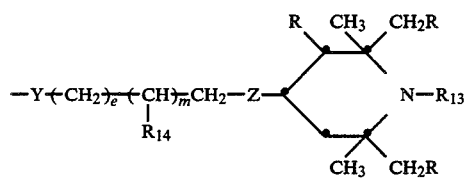

or of the formula

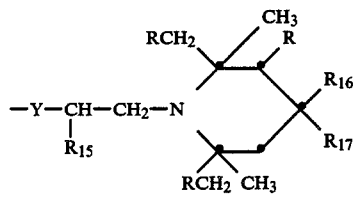

Color-forming agents which are obtained by imagewise exposure and development of this recording material for color photography are particularly stable towards the effect of visible and ultraviolet light.

Reference is made to the description in respect of the meanings of the substituents and symbols in the formulae.

17 Claims, No Drawings

RECORDING MATERIAL FOR COLOR PHOTOGRAPHY

This is a continuation-in-part application of copending application, Ser. No. 559,433, filed Dec. 8, 1983 (now abandoned).

The present application relates to a recording material for colour photography, which contains in at least one photosensitive silver halide emulsion layer and/or in at least one of the conventional auxiliary layers, a specific polyalkylpiperidine compound as a stabiliser.

Polyalkylpiperidines are sterically hindered amines which are generally known as light stabilisers for organic materials, especially for polymers. German Offenlegungsschrift No. 2,126,954 has also already proposed the use of such polyalkylpiperidines as agents against the fading of colour photographs. European Patent Application No. 11,051 has furthermore proposed the use of certain polyalkylpiperidine derivatives containing at least one phenol group as light stabilisers for colour photographs. These compounds are polyalkylpiperidine esters of hydroxybenzylmalonic acids.

It has now been found that polyalkylpiperidine compounds containing sterically hindered phenol linked via a carboxyl or carbamyl group where the polyalkylpiperidine radical is not bonded directly to the carboxyl or carbamyl group display a surprisingly better stabilising action.

The present invention thus relates to a recording material for colour photography, which contains in at least one photosensitive silver halide emulsion layer, one intermediate layer and/or one protective layer, at least one polyalkylpiperidine compound as a stabiliser, wherein the polyalkylpiperidine compound is of the formula I

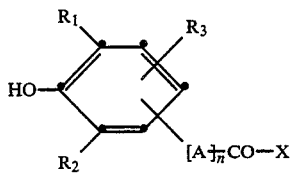

in which n is the number 0 or 1, $R_1$ is hydrogen, $C_1$–$C_8$-alkyl, $C_5$–$C_8$-cycloalkyl, phenyl, $C_7$–$C_{14}$-aralkyl, $C_7$–$C_{14}$-alkaryl or a group

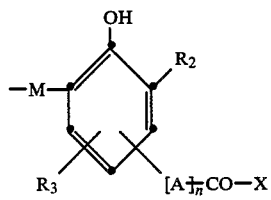

$R_2$ is $C_1$–$C_8$-alkyl, $C_5$–$C_8$-cycloalkyl, phenyl, $C_7$–$C_{14}$-aralkyl, $C_7$–$C_{14}$-alkaryl and $R_3$ is hydrogen or methyl, M is a direct bond, —S—, —S—S—, —S(O)—, —S-(O)$_2$— or —CH($R_4$)—, in which $R_4$ is hydrogen or $C_1$–$C_8$-alkyl, A is a group —CH$_2$—, —CH$_2$—CH($R_5$)—,

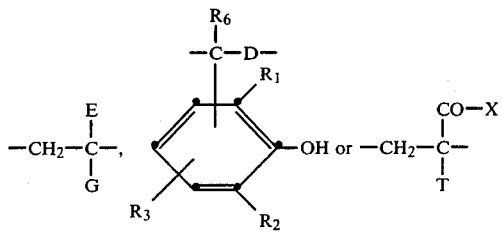

in which $R_5$ is hydrogen, methyl, ethyl, phenoxymethyl or phenyl, $R_6$ is hydrogen, $C_1$–$C_{12}$-alkyl, $C_5$–$C_8$-cycloalkyl, phenyl or benzyl, E is —CN or a group —COOR$_7$, —COR$_8$, —SO$_2$R$_8$, —P(O)(OR$_9$)$_2$ or —CHO, in which $R_7$ is $C_1$–$C_4$-alkyl, $R_8$ is $C_1$–$C_{12}$-alkyl, $C_7$–$C_{14}$-alkaryl or phenyl and $R_9$ is $C_1$–$C_{18}$-alkyl, phenyl or allyl, G is hydrogen, $C_1$–$C_{18}$-alkyl, $C_3$–$C_{12}$-alkenyl, $C_3$–$C_4$-alkinyl, $C_3$–$C_{12}$-cycloalkyl, $C_6$–$C_{18}$-alkylcycloalkyl, $C_6$–$C_{14}$-cycloalkylalkyl, $C_7$–$C_{14}$-aralkyl, $C_7$–$C_{14}$-alkaryl or phenyl or $C_1$–$C_{18}$-alkyl which is substituted by phenoxy, $C_7$–$C_{10}$-alkylphenoxy, benzyloxy, cyclohexyloxy, cyano, —COOR$_{10}$, —OCOR$_{11}$ or —P(O)(OR$_{12}$)$_2$, in which $R_{10}$ is $C_1$–$C_{18}$-alkyl, $C_3$–$C_{12}$-cycloalkyl or a group of the formula II

$+(C_aH_{2a})-CO-X$     (II)

in which a is an integer of from 1 to 6, $R_{11}$ is $C_1$–$C_{18}$-alkyl, $C_3$–$C_{12}$-cycloalkyl, phenyl, $C_7$–$C_9$-phenylalkyl or a group of the formula III

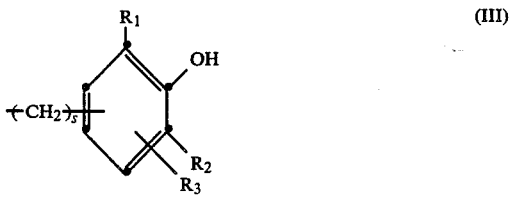

in which s is 0, 1 or 2, and $R_{12}$ is $C_1$–$C_8$-alkyl, allyl or phenyl, or G is $C_2$–$C_{18}$ alkyl which is interrupted by —O—, —S—, —SO— or —SO$_2$—, or is a group of the formula III, or, if E is a group —COR$_8$, G and $R_8$ together are tri- or tetra-methylene which is unsubstituted or substituted by hydroxyl or oxo, D is a group

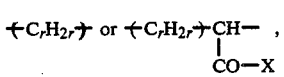

in which r is 0 or an integer of from 1 to 12, T is hydrogen, $C_1$–$C_{18}$-alkyl, $C_3$–$C_{12}$-alkenyl, $C_3$–$C_4$-alkinyl, $C_3$–$C_{12}$-cycloalkyl, $C_6$–$C_{18}$-alkylcycloalkyl, $C_6$–$C_{14}$-cycloalkylalkyl, $C_7$–$C_{14}$-aralkyl, $C_7$–$C_{14}$-alkaryl, phenyl, cyano or a group —COR$_8$, —SO$_2$R$_8$ or —P(O)(OR$_9$)$_2$, a group of the formula III or a group of the formula

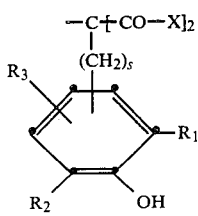

or T is $C_1-C_{18}$-alkyl which is interrupted by —O—, —S—, —SO— or —SO$_2$—, X is a group of the formula

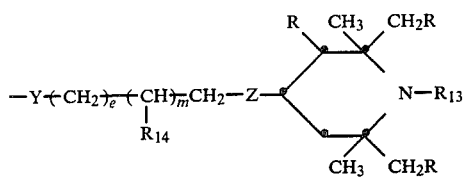

or of the formula

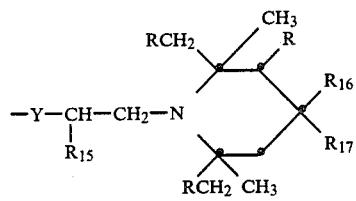

in which e is an integer of from 1 to 5, m is 0 or 1, R is hydrogen or methyl, $R_{13}$ is hydroxyl, $C_1-C_{12}$-alkyl, $C_3-C_6$-alkenylmethyl, $C_3-C_4$-alkinylmethyl, $C_7-C_{14}$-aralkyl or glycidyl, or $C_1-C_4$-alkyl which is substituted by halogen, cyano, —COOR$_{18}$ or —CON(R$_{19}$)(R$_{20}$), or a group —COR$_{21}$, —COOR$_{18}$ or —CON(R$_{19}$)—(R$_{20}$), a group —CH$_2$—CH(R$_{22}$)—OR$_{23}$, —SOR$_{24}$, —SO$_2$R$_{24}$, —OR$_{18}$ or —OCOR$_{21}$, in which R$_{18}$ is $C_1-C_{12}$-alkyl, allyl, cyclohexyl or benzyl, R$_{19}$ is $C_1-C_{12}$-alkyl, allyl, cyclohexyl, benzyl, phenyl or $C_7-C_{10}$-alkylphenyl and R$_{20}$ is hydrogen, $C_1-C_{12}$-alkyl, allyl, cyclohexyl or benzyl, or R$_{19}$ and R$_{20}$, together with the N atom to which they are bonded, are a 5-membered or 6-membered heterocyclic ring, R$_{21}$ is hydrogen, $C_1-C_{12}$-alkyl, $C_2-C_6$-alkenyl, chloromethyl, $C_5-C_8$-cycloalkyl, $C_7-C_{14}$-aralkyl, phenyl or $C_7-C_{10}$-alkylphenyl, or phenyl, phenylmethyl or phenylethyl which is substituted by 1 or 2 $C_1-C_4$-alkyl groups and 1 hydroxyl group, R$_{22}$ is hydrogen, $C_1-C_4$-alkyl, $C_3-C_4$-alkoxyalkyl, phenyl or phenoxymethyl, R$_{23}$ is hydrogen, $C_1-C_{12}$-alkyl or a group —COR$_{21}$ or —CON(R$_{19}$)(R$_{20}$) and R$_{24}$ is $C_1-C_{12}$-alkyl, phenyl or $C_7-C_{10}$-alkylphenyl, Y is —O— or —N(R$_{25}$)—, in which R$_{25}$ is hydrogen, $C_1-C_{18}$-alkyl, $C_3-C_{12}$-alkenyl, $C_3-C_{12}$-cycloalkyl, phenyl, $C_7-C_{14}$-aralkyl, $C_7-C_{14}$-alkaryl, $C_2-C_{11}$-alkoxyalkyl or a group of the formula IV, Z is —O— or —N(R$_{26}$)—, in which R$_{26}$ is hydrogen, $C_1-C_{18}$-alkyl, $C_3-C_{12}$-alkenyl, $C_3-C_{12}$-cycloalkyl, phenyl, $C_7-C_{14}$-alkaryl, $C_7-C_{14}$-aralkyl, $C_2-C_{11}$-alkoxyalkyl or a group —COR$_{27}$, —COOR$_{28}$, —CON(R$_{29}$)(R$_{30}$), —CH$_2$—CH(R$_{31}$)—OR$_{32}$, —SOR$_{33}$ or —SO$_2$R$_{33}$, in which R$_{27}$ has one of the meanings given for R$_{21}$ or is a heterocyclic ring, R$_{28}$ has one of the meanings given for R$_{18}$, R$_{29}$ has one of the meanings given for R$_{19}$, R$_{30}$ has one of the meanings given for R$_{20}$, R$_{31}$ has one of the meanings given for R$_{22}$, R$_{32}$ has one of the meanings given for R$_{23}$ and R$_{33}$ has one of the meanings given for R$_{24}$, or R$_{26}$ is one of the groups

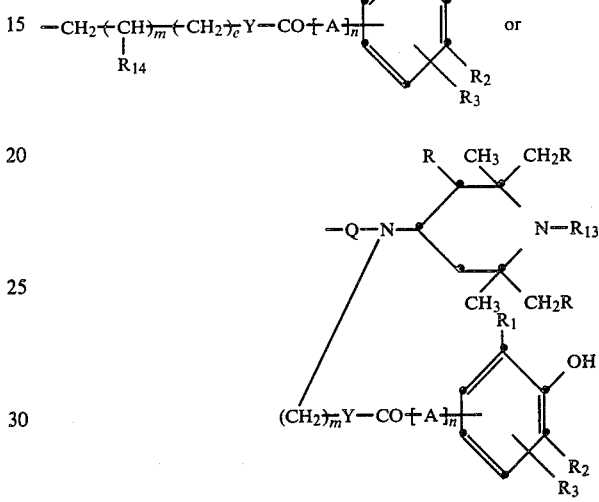

Q is a group —(C$_b$H$_{2b}$)—, in which b is an integer of from 2 to 12, $C_4-C_8$-alkenylene, $C_5-C_{12}$-cycloalkylene, phenylene, xylylene bitolylene, a group —CO—(C$_r$H$_{2r}$)—CO—,

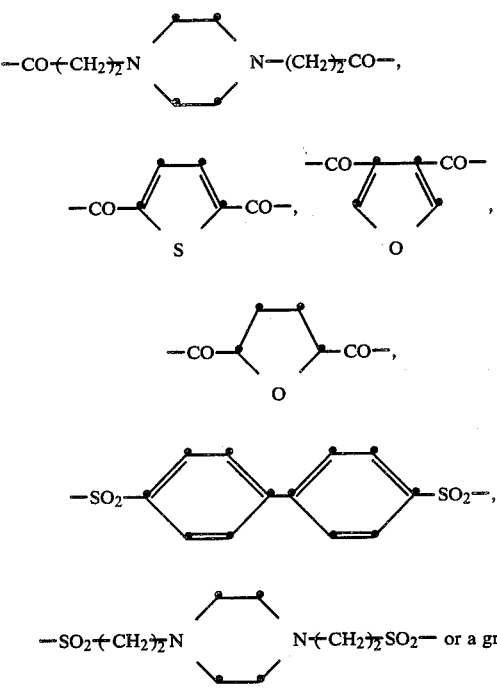

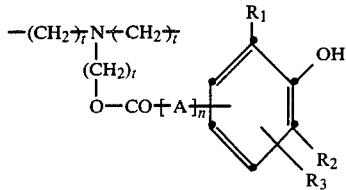

in which t is 0 or an integer of from 1 to 5, or $R_{13}$ is a group of the formula

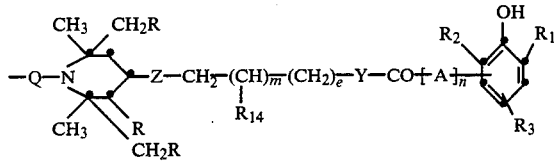

and $R_{14}$ is hydrogen, $C_1$–$C_{18}$-alkyl, $C_7$–$C_{23}$-phenoxyalkyl, phenyl, $C_7$–$C_{14}$-aralkyl or $C_2$–$C_{11}$-alkoxyalkyl, $R_{15}$ is hydrogen, methyl, ethyl, phenyl or phenoxymethyl, $R_{16}$ is hydrogen, —$OR_{34}$, —$OCOR_{35}$, —$N(R_{3-6})$—$COR_{35}$, —$OSO_2R_{35}$ or —$N(R_{36})$—$SO_2R_{35}$, in which $R_{34}$ is hydrogen, $C_1$–$C_{12}$-alkyl allyl or benzyl, $R_{35}$ is hydrogen, $C_1$–$C_{12}$-alkyl, $C_2$–$C_6$-alkenyl, chloromethyl, $C_5$–$C_8$-cycloalkyl, $C_7$–$C_9$-phenylalkyl, $C_7$–$C_{10}$-alkylphenyl, phenyl or a group

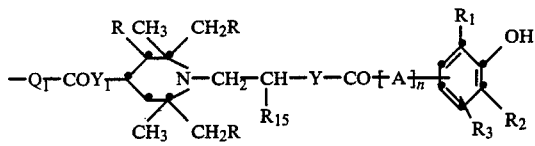

in which $Y_1$ has one of the meanings given for Y, $Q_1$ is a group —($C_rH_{2r}$)—, $C_2$–$C_8$-alkenylene, $C_5$–$C_{12}$-cycloalkylene, phenylene, xylylene, bitolylene or a group

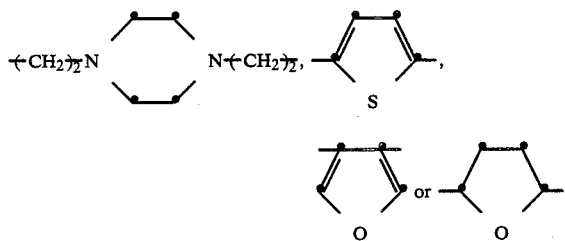

and $R_{36}$ is hydrogen, $C_1$–$C_{12}$-alkyl, $C_5$–$C_8$-cycloalkyl or benzyl, and $R_{17}$ is hydrogen, cyano, —$COOR_{18}$, —$CONH_2$, —$CON$—$(R_{19})(R_{20})$ or —$CH_2NHR_{37}$, in which $R_{37}$ is a group —$COR_{21}$ —$COOR_{18}$, —$CON(R_{19})(R_{20})$, —$CH_2$—$CH(R_{22})$—$OR_{23}$, —$SOR_{24}$ or —$SO_2R_{24}$, the radicals and symbols mentioned repeatedly always being as first defined.

Any alkyl substituents are straight-chain or branched alkyl groups. $C_1$–$C_4$-alkyl groups are then methyl, ethyl, n-propyl, isopropyl, n-butyl, sec.-butyl or tert.-butyl. Examples of $C_1$–$C_8$-alkyl groups are, in addition, n-pentyl, 2,2-dimethylpropyl, n-hexyl, 2,3-dimethylbutyl, n-octyl and 1,1,3,3-tetramethylbutyl. Examples of $C_1$–$C_{12}$-alkyl groups are, in addition, also nonyl, decyl, undecyl and dodecyl. Additional examples of $C_1$–$C_{18}$-alkyl are tetradecyl, hexadecyl, heptadecyl and octadecyl.

Any $C_5$–$C_8$-cycloalkyl substituents are, for example, cyclopentyl, cyclohexyl, cycloheptyl, α-methylcyclohexyl, cyclooctyl or dimethylcyclohexyl. Additional examples of $C_3$–$C_{12}$-cycloalkyl are cyclopropyl, cyclononyl, cyclodecyl and cyclododecyl. Cyclohexyl is preferred.

$C_7$–$C_9$-Phenylalkyl $R_{11}$ or $R_{35}$ is, for example, benzyl, phenylethyl or phenylpropyl. Any $C_7$–$C_{14}$-aralkyl substituents are furthermore, for example, also phenylbutyl or naphthylmethyl.

Any $C_7$–$C_{10}$-alkylphenyl substituents can be, for example, tolyl, xylyl, isopropylphenyl, tert.-butylphenyl or diethylphenyl.

$C_3$–$C_6$-Alkenylmethyl $R_{13}$ is, for example, allyl, methallyl, dimethylallyl or 2-hexenyl. $C_2$–$C_6$-Alkenyl $R_{21}$, $R_{27}$ or $R_{35}$ can additionally also be vinyl.

$C_3$–$C_{12}$-Alkenyl G, T, $R_{25}$ or $R_{26}$ can be, for example allyl, methallyl, 2-butenyl, 2-hexenyl, 2-octenyl, 4-octenyl, 2-decenyl or 2-dodecenyl. Allyl is preferred.

$C_3$–$C_4$-Alkinyl G or T and $C_3$–$C_4$-alkinylmethyl $R_{13}$ are, for example, propargyl, n-but-4-inyl or n-but-2-inyl. Propargyl is preferred.

Any $C_7$–$C_{14}$-alkaryl substituents are, for example, phenyl which is substituted by $C_1$–$C_4$-alkyl, such as p-tolyl, 2,4-dimethylphenyl, 2,6-dimethylphenyl, 2,4-diethylphenyl, 2,6-diethylphenyl, 4-tert.-butylphenyl, 2,4-di-tert.-butylphenyl or 2,6-di-tert.-butylphenyl. 2,4-Di-tert.-butylphenyl and 2,4-dimethylphenyl are preferred.

$C_3$–$C_4$-Alkoxyalkyl $R_{22}$ or $R_{31}$ is, for example, ethoxymethyl, 2-methoxyethyl or 2-ethoxyethyl. $C_2$–$C_{11}$-Alkoxyalkyl $R_{14}$, $R_{25}$ or $R_{26}$ can moreover also be methoxymethyl, 2-n-butoxyethyl, 2-n-butoxypropyl, 2-n-octoxyethyl, 3-n-octoxypropyl or 6-n-butoxyhexyl.

$C_7$–$C_{23}$-Phenoxyalkyl $R_{14}$ is, for example, phenoxymethyl, phenoxyethyl, phenoxypropyl, phenoxybutyl, phenoxyoctyl, phenoxydecyl, phenoxydodecyl or phenoxyhexadecyl.

$C_4$–$C_8$-Alkenylene Q or $Q_1$ is, for example, 2-but-1,4-enylene.

$C_5$–$C_{12}$-Cycloalkylene Q or $Q_1$ is, for example, cyclopentylene, cyclohexylene, cyclooctylene, cyclodecylene or cyclododecylene. Cyclohexylene is preferred.

Any halogen substituents are, for example, bromine, iodine or, in particular, chlorine.

$C_1$–$C_4$-Alkyl $R_{13}$ which is substituted by halogen, cyano, —$COOR_{18}$ or —$CON(R_{19})(R_{20})$ is, for example, chloromethyl, 1-chloroethyl, 2-chloroethyl, 3-chloropropyl, 4-chlorobutyl, bromomethyl, iodomethyl, cyanomethyl, methoxycarbonylmethyl, N,N'-dimethylaminocarbonylmethyl or 2-chloro-2-methylpropyl.

$C_1$–$C_{18}$-Alkyl G which is substituted by phenoxy, benzyloxy, cyclohexyloxy or cyano can be, for example, one of the following radicals: 2-phenoxyethyl, 2-benzyloxyethyl, cyclohexyloxymethyl, 2-cyanoethyl, cyanomethyl or 3-cyanopropyl.

$C_6$–$C_{18}$-Alkylcycloalkyl G or T is, for example, methylcyclohexyl, ethylcyclohexyl, butylcyclohexyl, tert.-butylcyclohexyl, dodecylcyclohexyl, ethylcyclopentyl or butylcyclopentyl, and $C_6$–$C_{14}$-cycloalkylalkyl G or T is, for example, cyclohexylmethyl, cyclohexylethyl, cyclohexylbutyl, cyclohexylhexyl, cyclohexyloctyl, cyclopentylpropyl or cyclopentylhexyl.

$C_1$–$C_{18}$-Alkyl G which is substituted by $C_7$–$C_{10}$-alkyphenoxy can be, for example, p-methylphenoxymethyl, p-methylphenoxyethyl, p-methylphenoxypropyl, p- tert.-butylphenoxymethyl, p-tert.-butylphenoxyethyl, 2,4-dimethylphenoxymethyl, 2,4-dimethylphenoxyethyl, 2,4-di-tert.-butylphenoxyethyl, 2,6-di-tert.-butylphenoxymethyl or 2,4,6-trimethylphenoxyethyl.

$C_2-C_{18}$-Alkyl G or T which is interrupted by —O—, —S—, —SO— or —SO$_2$— is, for example, one of the following radicals: methoxymethyl, 2-butoxyethyl, 2-octyloxyethyl, isopropoxymethyl, 3-butylthiopropyl, 2-decylthioethyl, 2-(isohexylsulfinyl)-ethyl, 2-(butylsulfonyl)-ethyl or 3-(ethylsulfonyl)propyl.

Phenyl, phenylmethyl or phenethyl $R_{21}$ or $R_{27}$ which is substituted by 1 or 2 $C_1-C_4$-alkyl radicals and 1 hydroxyl group is, for example, 2,5-dimethyl-4-hydroxyphenyl, 3,5-di-tert.-butyl-4-hydroxyphenyl, 3,5-dimethyl-4-hydroxybenzyl, 3,5-di-tert.-butyl-4-hydroxybenzyl or 2-(3,5-di-tert.-butyl-4-hydroxyphenyl)-ethyl.

In a group —$C_rH_{2r}$— D, Q or $Q_1$ in which r is a number between 1 and 12, r is preferably a number between 2 and 8. Examples are methylene, ethylene, trimethylene, tetramethylene, hexamethylene, octamethylene, nonamethylene, 2,2,4-trimethylhexamethylene, decamethylene or dodecamethylene.

A heterocyclic ring $R_{27}$ is, for example, pyridine, quinoline, pyrimidine, thiazole, imidazole, oxazole, pyrrolidine, piperazine, morpholine, piperidine, furan, tetrahydrofuran, thiophene, pyrrole or indole.

Preferred recording materials for colour photography are those which contain, as the stabiliser, at least one compound of the formula I, wherein Z is —N(R')— and in which R' is a group —$COR_{27}$, —$COOR_{28}$, —$CON(R_{29})(R_{30})$, —$SOR_{33}$ or —$SO_2R_{33}$ and the symbols $R_{27}$, $R_{28}$, $R_{29}$, $R_{30}$ and $R_{33}$ have one of the meanings as given before, and particularly preferred are those, wherein $R_{13}$ is a group —$COR_{21}$, —$COOR_{18}$, —$CON(R_{19})(R_{20})$, —$SOR_{24}$ or —$SO_2R_{24}$ and the symbols $R_{21}$, $R_{18}$, $R_{19}$, $R_{20}$ and $R_{24}$ have one of the meanings as given before.

Further preferred recording materials for colour photography are those which contain, as the stabiliser, at least one compound of the formula I in which A is a group —CH$_2$—, —CH$_2$—CH(R$_5$)—,

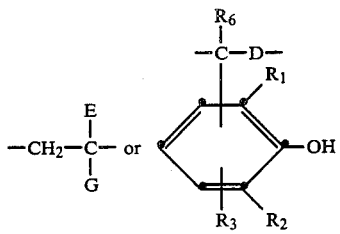

Preferred recording materials for colour photography are those which contain, as the stabiliser, at least one compound of the formula V

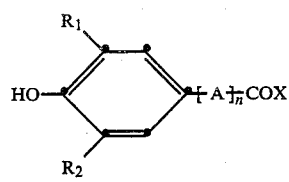

(V)

in which n is the number 0 or 1, $R_1$ is hydrogen or $C_1-C_4$-alkyl, $R_2$ is $C_1-C_4$-alkyl, A is a group —CH$_2$—, —CH$_2$—CH(R$_5$)—

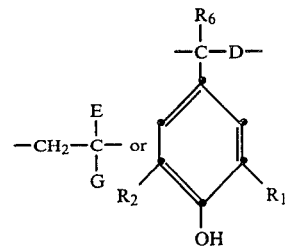

in which $R_5$ and $R_6$ are hydrogen or methyl, E is cyano, —COCH$_3$ or —COOCH$_3$, G is hydrogen, $C_1-C_{18}$-alkyl, allyl, cyclohexyl, benzyl or a group

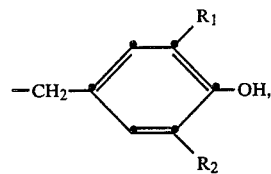

or E and G together are a group —CO—(CH$_2$)$_4$, D is a group —($C_rH_{2r}$)—, in which r is 0 or an integer of from 1 to 6, and X is a group of the formula

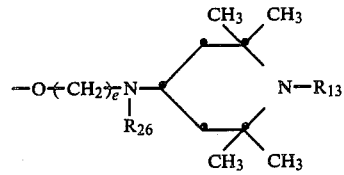

or of the formula

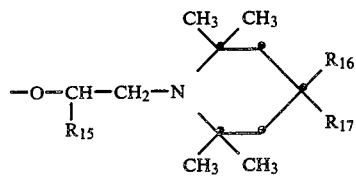

in which e is an integer of from 2 to 3, $R_{13}$ is hydroxyl, methyl, allyl, benzyl, 2-hydroxyethyl, acetyl, acroyl or a group of the formula —CON(R$_{19}$)R$_{20}$), in which $R_{19}$ is $C_1-C_8$-alkyl, cyclohexyl or phenyl and $R_{20}$ is hydrogen or $C_1-C_{12}$-alkyl, $R_{26}$ is hydrogen, $C_1-C_8$-alkyl or a group —$COR_{27}$, —$COOR_{28}$, —CO-N—(R$_{29}$)(R$_{30}$), —CH$_2$—CH(R$_{31}$)—OR$_{32}$ or —SO$_2$R$_{33}$, in which $R_{27}$ is $C_1-C_{12}$-alkyl, $C_2-C_4$-alkenyl, cyclohexyl, benzyl, phenyl, 2-(3,5-di-tert.-butyl-4-hydroxyphenyl)-ethyl or a heterocyclic ring, $R_{28}$ is $C_1-C_8$-alkyl, allyl or cyclohexyl, $R_{29}$ is $C_1-C_{12}$-alkyl, cyclohexyl or phenyl and $R_{30}$ is hydrogen or $C_1-C_{12}$-alkyl, or $R_{29}$ and $R_{30}$, together with the N atom to which they are bonded, are a 6-membered heterocyclic ring, $R_{31}$ is hydrogen, methyl or phenyl and $R_{32}$ is hydrogen, $C_1-C_4$-alkyl or a group —$COR_{21}$ or —CON(R$_{19}$)(R$_{20}$) and $R_{33}$ is $C_1-C_{12}$-alkyl, phenyl or $C_7-C_{10}$-alkylphenyl, $R_{15}$ is hydrogen, methyl or phenyl, $R_{16}$ is hydrogen, —OR$_{34}$, —OCOR$_{35}$, or —N(R$_{36}$)—COR$_{35}$, in which $R_{34}$ is hydrogen, $C_1-C_8$-alkyl, allyl, benzyl or phenyl, $R_{35}$ is hydrogen, $C_1-C_8$-alkyl, allyl, benzyl or phenyl and $R_{36}$ is hydrogen, $C_1-C_4$-alkyl, cyclohexyl or benzyl, and $R_{17}$ is hydrogen, cyano, —$COOR_{18}$, —$CONH_2$, —CON—$(R_{19})(R_{20})$ or —$CH_2NHR_{37}$, in which $R_{37}$ is a group —$COR_{21}$, —$COOR_{18}$, —$CON(R_{19})(R_{20})$ or —$CH_2$—$CH(R_{22})$—$OR_{23}$, the radicals and symbols repeatedly mentioned in this preferred meaning always being as first defined in this preferred meaning.

Particularly preferred recording materials for colour photography are those which contain, as the stabiliser, at least one compound of the formula V in which n is 0 or 1, $R_1$ is hydrogen, methyl or tert.-butyl, $R_2$ is methyl or tert.-butyl, A is a group —$CH_2$— or —$CH_2CH_2$—, in which X is a group of the formula

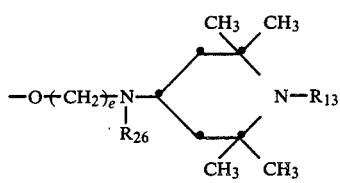

or of the formula

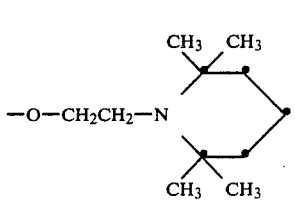

in which e is an integer of from 2 to 3, $R_{13}$ is methyl, allyl, benzyl, 2-hydroxyethyl, acetyl or acroyl and $R_{26}$ is hydrogen, $C_1$-$C_8$-alkyl or a group of the formula —$COR_{27}$ or —$SO_2R_{33}$, in which $R_{27}$ is $C_1$-$C_{12}$-alkyl or $C_2$-$C_4$-alkenyl and $R_{33}$ is $C_1$-$C_4$-alkyl, phenyl or p-tolyl.

The compounds of the formula I can be obtained analogously to known compounds, such as those described, for example, in German Offenlegungsschriften Nos. 2,456,864, 2,647,452, 2,654,058 and 2,656,769. The starting substances are known. Specific examples which are still novel can be obtained analogously to the known compounds.

The last stage of the synthesis is either direct esterification (acid+alcohol or acid chloride+alcohol), transesterification or amidation.

Typical representatives of compounds of the formula I are listed in Table I below.

TABLE I (structure: 2,6-di-tert-butyl-4-substituted phenol with HO—Ar—A—CO—X)

| Stabiliser No. | A | X |
|---|---|---|
| 1 | —$CH_2CH_2$— | —O$(CH_2)_2$N[tetramethylpiperidine with $COCH_3$ on N, N—$COCH_3$] |
| 2 | (structure with (CH$_3$)$_3$C, HO-phenyl, —$CH_2$—C(COX)(CH$_2$)) | —O$(CH_2)_2$N[tetramethylpiperidine with CO—CH=$CH_2CH_3$ on N, N—CO—CH=$CH_2$] |
| 3 | —CH— attached to 3,5-di-tert-butyl-4-hydroxyphenyl | —O$(CH_2)_2$N[tetramethylpiperidine with $COCH_3$ on N, N—$COCH_3$] |

TABLE I-continued
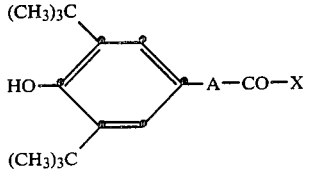
| Stabiliser No. | A | X |
|---|---|---|
| 4 | 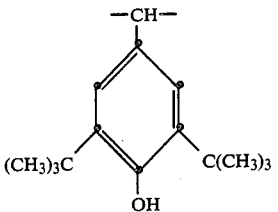 | 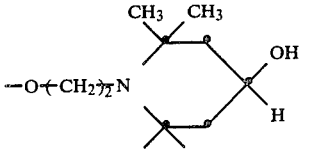 |
| 5 | —CH₂—CH₂— | 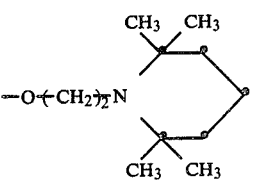 |
| 6 | 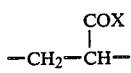 | 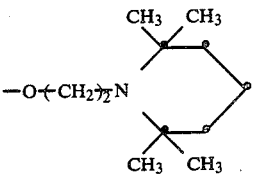 |
| 7 | —CH₂CH₂— | 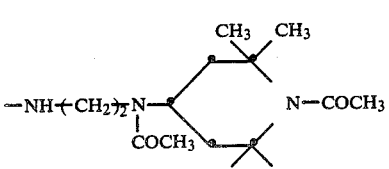 |
| 8 | —CH₂CH₂— | 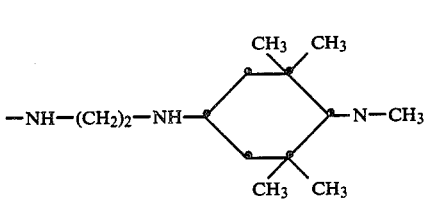 |
| 9 | — | 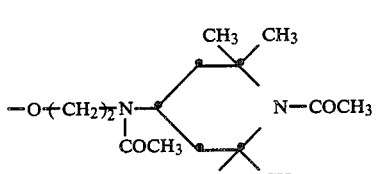 |
| 10 | — | 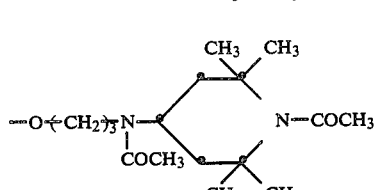 |

TABLE I-continued
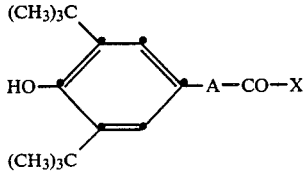
| Stabiliser No. | A | X |
|---|---|---|
| 11 | — | 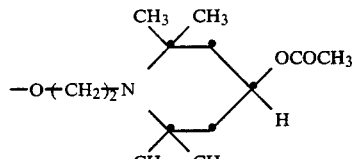 |
| 12 | — | 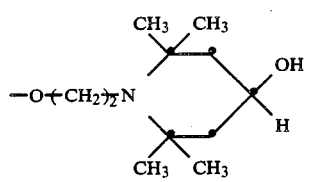 |
| 13 | —CH₂CH₂— | 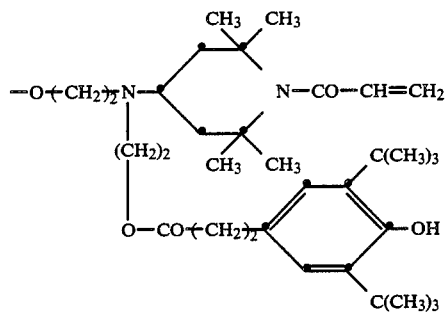 |
| 14 | —CH₂CH₂— | 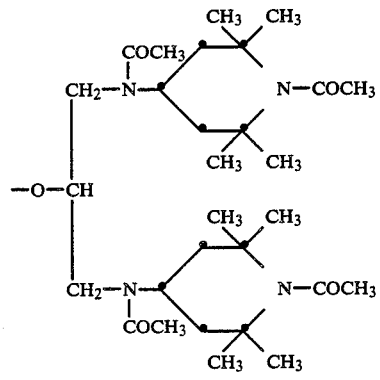 |
| 15 | —CH₂CH₂— | 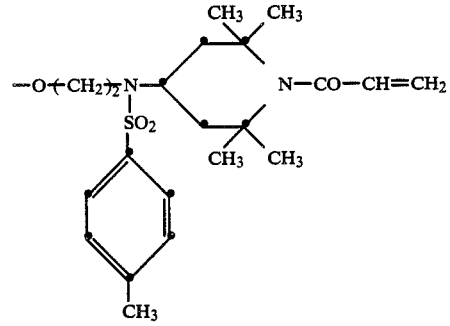 |

TABLE I-continued
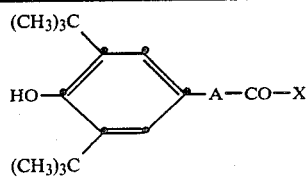
| Stabiliser No. | A | X |
|---|---|---|
| 16 | — | 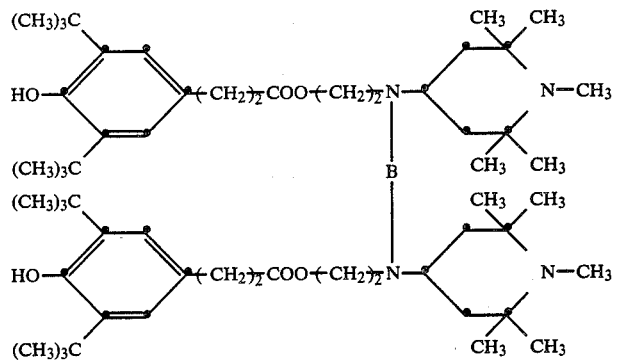 |
Other typical representatives of compounds of the formula I are the following:
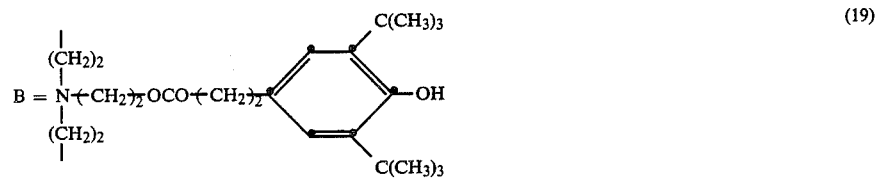
B = ―(CH₂)₆―  (17)
B = ―CO―(CH₂)₄―CO―  (18)
$$B = \underset{(CH_2)_2}{\overset{(CH_2)_2}{N}}\!\!-(CH_2)_2OCO-(CH_2)_2-\!\!\bigcirc\!\!-OH \quad (19)$$
(with C(CH₃)₃ groups ortho to OH)
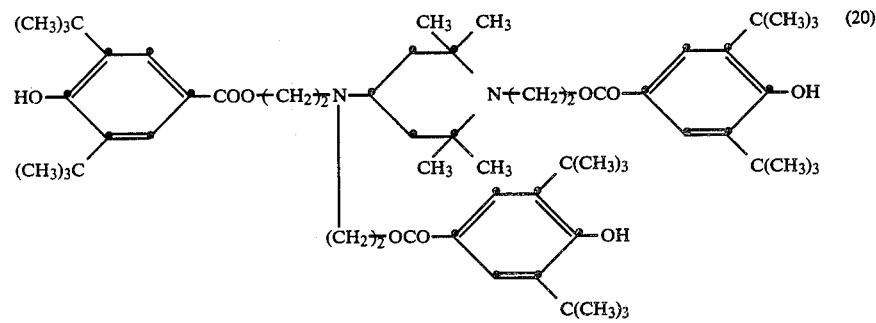
(20)

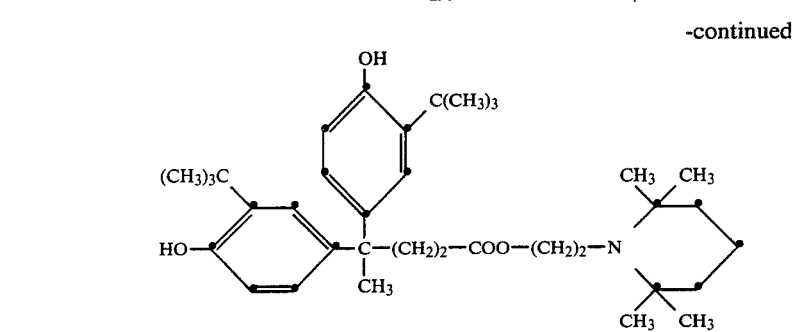
(21)
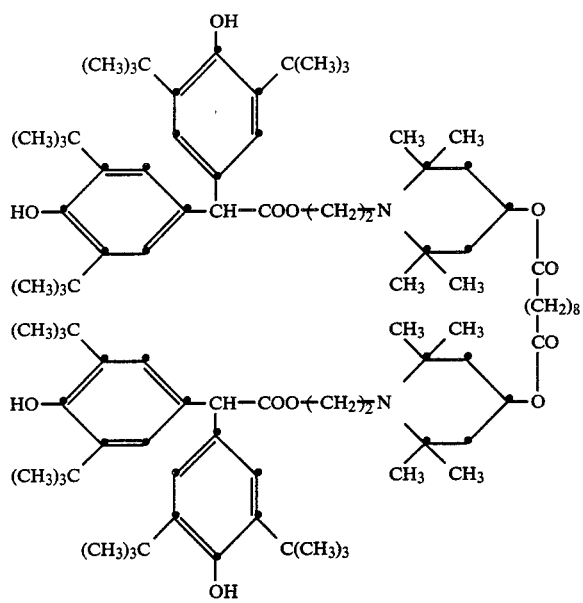
(22)
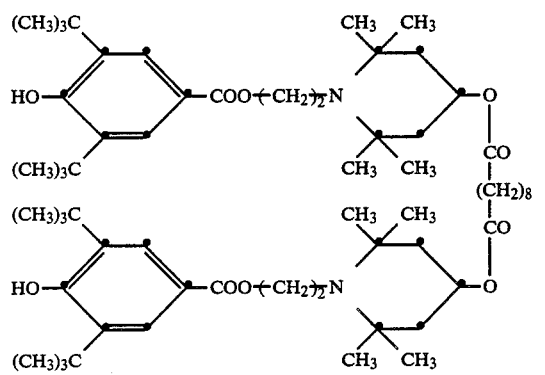
(23)
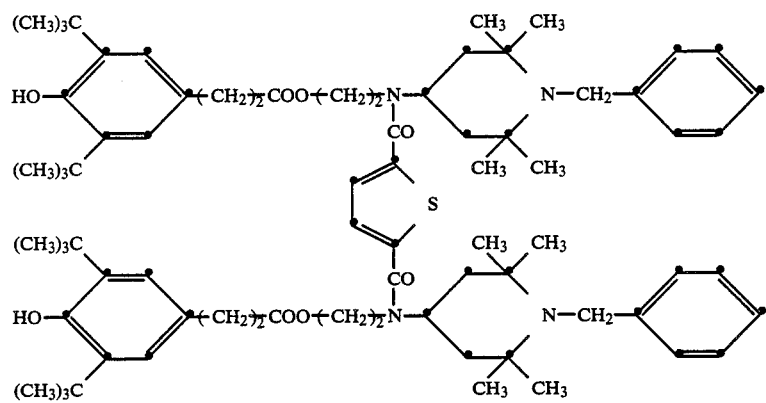
(24)

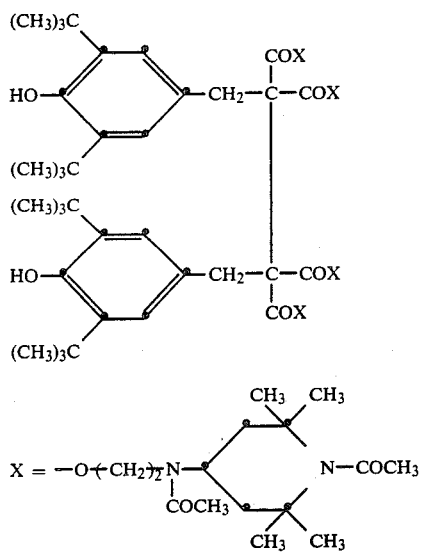

(25)

The stabilisers of the formula I can be incorporated into a photographic material in a conventional manner by themselves or together with other compounds.

The stabilisers are as a rule incorporated into the photographic material by themselves or together with other compounds, especially with colour couplers, in the form of a dispersion, this dispersion containing either no solvent or high-boiling or low-boiling solvents or a mixture of such solvents. A further suitable method of incorporation comprises incorporating the stabilisers into the photographic material by themselves or together with other compounds together with a polymer in the form of a latex.

The dispersions are then used for the preparation of the layers of recording materials for colour photography. These layers can be, for example, intermediate layers or protective layers, and especially photosensitive (blue-sensitive, green-sensitive and red-sensitive) silver halide emulsion layers in which the blue-green (cyano), purple (magenta) and yellow dyes are formed from the corresponding colour couplers on development of the exposed recording material.

The silver halide layers can contain any colour couplers, in particular blue-green, purple and yellow couplers, which are used for formation of the dyes mentioned and hence of the colour-forming agents.

Since the substrate influences the action and stability of the compounds of the formula I, substrates (solvents and polymers) which, together with these compounds, give as good as possible a resistance of the materials to be stabilised are preferred.

As a rule, the stabilisers of the formula I are incorporated into layers which additionally contain a silver halide dispersion prepared and sensitised by conventional methods. However, they can also be in layers adjacent to layers containing silver halide.

The photographic materials according to the invention have a conventional build-up and contain conventional components. However, a build-up and components which intensify the activity of the stabilisers of the formula I or at least do not adversely affect it are preferred.

The stabilisers according to the formula I can additionally also be combined with ultraviolet absorbers, other light stabilisers or stabilisers, besides with the colour couplers, in the same layer in the photographic recording material according to the present invention.

If the diffusion transfer method is applied, the stabiliser can also be incorporated into a receiver layer.

The materials, according to the invention, for colour photography can be processed in a known manner. Furthermore, during the course of or after processing, they can be treated in a manner such that their stability is increased further, for example they can be treated in a stabiliser bath or a protective coating can be applied.

In certain cases, the stabilisers to be used according to the invention are also suitable for the protection of layers, for colour photography, in which the dyes are incorporated directly into the emulsion and the image is produced by selective bleaching.

The amount of stabiliser or stabilisers can vary within wide limits and is approximately in the range from 1 to 2,000 mg, preferably 100 to 800 mg and in particular 200–500 mg, per $m^2$ of the layer in which it (they) is (are) incorporated.

If the photographic material contains an agent which absorbs UV radiation, this can be present together with the stabiliser in one layer or in an adjacent layer. The amount of UV absorber or UV absorbers can vary within wide limits and is approximately in the range from 200–2,000 mg/$m^2$, preferably 400–1,000 mg/$m^2$, of the layer in which it (they) is (are) incorporated.

Examples of ultraviolet absorbers are compounds of the benzophenone, acrylonitrile, thiazolidone, benzotriazole, oxazole, thiazole and imidazole type.

The colour-forming agents obtained with the recording material according to the invention by exposure and development have a very good light-fastness towards visible and ultraviolet light. The compounds of the formula I are virtually colourless, so that no discolouration of the images occurs; in addition, they are highly compatible with the conventional photographic additives present in the individual layers. On the basis of their good activity, the amount thereof employed can be reduced, and precipitation or crystallisation of the compounds is thus avoided if they are incorporated as an organic solution into the aqueous binder emulsions used for the preparation of photographic layers. The individual processing steps required after exposure of the photographic recording material for the preparation of the colour-forming agents are not adversely affected by the stabilisers of the formula I. Furthermore, the so-called print fogging which frequently occurs with blue-sensitive emulsions can be substantially suppressed. This fogging can occur, for example, if photographic materials (silver halide emulsion layers on a carrier of natural or synthetic materials) are subjected to mechanical stress, for example rotation, bending or rubbing, during preparation or during the treatment before the development. (T. H. James, The Theory of Photographic Process, 4th Edition, Macmillan, New York, N.Y. 1977, pages 23 et seq., pages 166 et seq.).

USE EXAMPLES 0.087 g of the yellow coupler of the formula

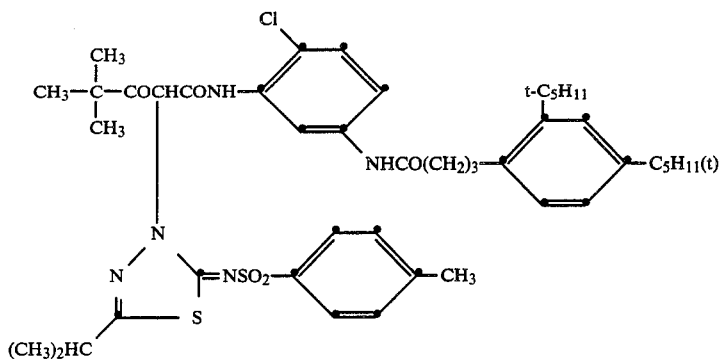

and 0.026 g of one of the light stabilisers shown in the table below are dissolved in 2.0 ml of a mixture of tricresylphosphate/ethyl acetate (1.5 g in 100 ml). 7.0 ml of a 6% gelatin solution, 0.5 ml of an 8% solution of the wetting agent of the formula

in isopropanol/water (3:4) and 0.5 ml of water are added to this solution and the mixture is emulsified with ultrasound at an output of 100 Watt for 5 minutes.

2.0 ml of a silver bromide emulsion with a silver content of 6.0 per liter, 0.7 ml of a 1% aqueous solution of the hardener of the formula

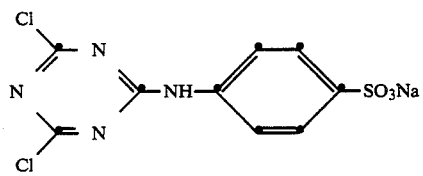

and 3.8 ml of water are added to 2.5 ml of the emulsion thus obtained, and the mixture is adjusted to a pH value of 6.5 and poured onto subbed plastic-coated white paper mounted up on a glass plate.

After solidification, the layer is dried in a circulating air drying cabinet at room temperature.

After 7 days, samples cut to 35×180 mm are exposed behind a step wedge at 3,000 Lux.s and are then processed by the Ektaprint 2 ® process of Kodak.

The yellow wedges thus obtained are irradiated in an Atlas Weather-meter with a 2,500 W Xenon lamp with a total of 42 kJoules/cm$^2$ (a comparison sample contains no light stabiliser).

The loss in colour density which thereby occurs is determined by measuring the colour density at $\lambda_{max}$ with a Densitometer ®TR 924 A from Macbeth.

The results are shown in the table below:

| Light stabiliser No. | Density loss at the maximum of reflection in percent |
|---|---|
| — | 36 |
| 1 | 17 |
| 9 | 17 |
| 15 | 15 |
| 16 | 15 |
| 20 | 18 |

What is claimed is:

1. A recording material for color photography, which contains in at least one photosensitive silver halide emulsion layer, one intermediate layer and/or one protective layer, a light stabilising amount of at least one polyalkylpiperidine compound as a stabiliser, wherein the polyalkylpiperidine compound is of the formula I

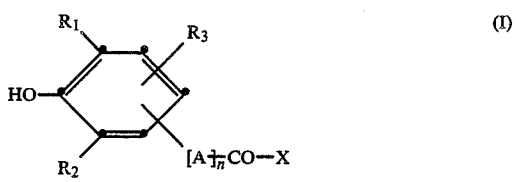

in which n is 0 or 1, $R_1$ is hydrogen, $C_1-C_8$-alkyl, $C_5-C_8$-cycloalkyl, phenyl, $C_7-C_{14}$-aralkyl, $C_7-C_{14}$-alkaryl or a group

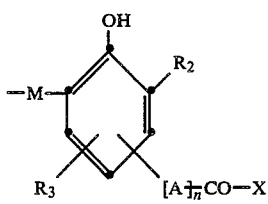

$R_2$ is $C_1-C_8$-alkyl, $C_5-C_8$-cycloalkyl, phenyl, $C_7-C_{14}$-aralkyl, $C_7-C_{14}$-alkaryl and $R_3$ is hydrogen or methyl, M is a direct bond, —S—, —S—S—, —S(O)—, —S(O)$_2$— or —CH(R$_4$)—, in which R$_4$ is hydrogen or $C_1$–$C_8$-alkyl, A is a group —$CH_2$—, —$CH_2$—$CH(R_5)$—,

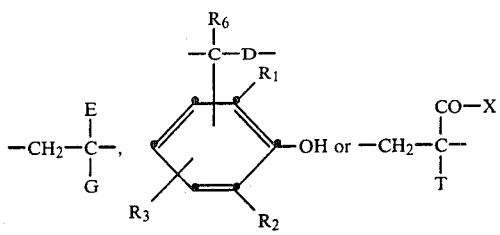

in which $R_5$ is hydrogen, methyl, ethyl, phenoxymethyl or phenyl, $R_6$ is hydrogen, $C_1$–$C_{12}$-alkyl, $C_5$–$C_8$-cycloalkyl, phenyl or benzyl, E is —CN or a group —$COOR_7$, —$COR_8$, —$SO_2R_8$, —$P(O)(OR_9)_2$ or —CHO, in which $R_7$ is $C_1$–$C_4$-alkyl, $R_8$ is $C_1$–$C_{12}$-alkyl, $C_7$–$C_{14}$-alkaryl or phenyl and $R_9$ is $C_1$–$C_{18}$-alkyl, phenyl or allyl, G is hydrogen, $C_1$–$C_{18}$-alkyl, $C_3$–$C_{12}$-alkenyl, $C_3$–$C_4$-alkinyl, $C_3$–$C_{12}$-cycloalkyl, $C_6$–$C_{18}$-alkylcycloalkyl, $C_6$–$C_{14}$-cycloalkylalkyl, $C_7$–$C_{14}$-aralkyl, $C_7$–$C_{14}$-alkaryl or phenyl or $C_1$–$C_{18}$-alkyl which is substituted by phenoxy, $C_7$–$C_{10}$-alkylphenoxy, benzyloxy, cyclohexyloxy, cyano, —$COOR_{10}$, —$OCOR_{11}$ or —$P(O)(OR_{12})_2$, in which $R_{10}$ is $C_1$–$C_{18}$-alkyl, $C_3$–$C_{12}$-cycloalkyl or a group of the formula II

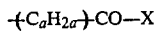  (II)

in which a is an integer of from 1 to 6, $R_{11}$ is $C_1$–$C_{18}$-alkyl, $C_3$–$C_{12}$-cycloalkyl, phenyl, $C_7$–$C_9$-phenylalkyl or a group of the formula III

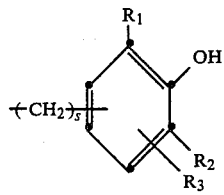  (III)

in which s is 0, 1 or 2, and $R_{12}$ is $C_1$–$C_8$-alkyl, allyl or phenyl, or G is $C_2$–$C_{18}$-alkyl which is interrupted by —O—, —S—, —SO— or —$SO_2$—, or is a group of the formula III, or, if E is a group —$COR_8$, G and $R_8$ together are tri- or tetra-methylene which is unsubstituted or substituted by hydroxyl or oxo, D is a group

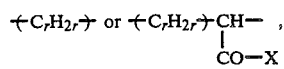

in which r is 0 or an integer of from 1 to 12, T is hydrogen, $C_1$–$C_{18}$-alkyl, $C_3$–$C_{12}$-alkenyl, $C_3$–$C_4$-alkinyl, $C_3$–$C_{12}$-cycloalkyl, $C_6$–$C_{18}$-alkylcycloalkyl, $C_6$–$C_{14}$-cycloalkylalkyl, $C_7$–$C_{14}$-aralkyl, $C_7$–$C_{14}$-alkaryl, phenyl, cyano or a group —$COR_8$, —$SO_2R_8$ or —$P(O)(OR_9)_2$, a group of the formula III or a group of the formula

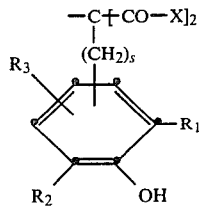

or T is $C_1$–$C_{18}$-alkyl which is interrupted by —O—, —S—, —SO— or —$SO_2$—, X is a group of the formula

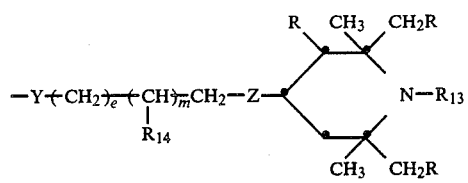

or of the formula

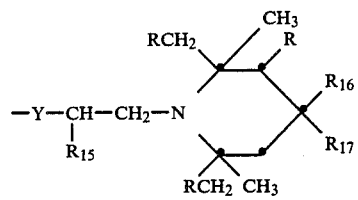

in which e is an integer of from 1 to 5, m is 0 or 1, R is hydrogen or methyl, $R_{13}$ is hydroxyl, $C_1$–$C_{12}$-alkyl, $C_3$–$C_6$-alkenylmethyl, $C_3$–$C_4$-alkinylmethyl, $C_7$–$C_{14}$-aralkyl or glycidyl, or $C_1$–$C_4$-alkyl which is substituted by halogen, cyano, —$COOR_{18}$ or —$CON(R_{19})(R_{20})$, or a group —$COR_{21}$, —$COOR_{18}$ or —$CON(R_{19})$—$(R_{20})$, a group —$CH_2$—$CH(R_{22})$—$OR_{23}$, —$SOR_{24}$, —$SO_2R_{24}$, —$OR_{18}$ or —$OCOR_{21}$, in which $R_{18}$ is $C_1$–$C_{12}$-alkyl, allyl, cyclohexyl or benzyl, $R_{19}$ is $C_1$–$C_{12}$-alkyl, allyl, cyclohexyl, benzyl, phenyl or $C_7$–$C_{10}$-alkylphenyl and $R_{20}$ is hydrogen, $C_1$–$C_{12}$-alkyl, allyl, cyclohexyl or benzyl, or $R_{19}$ and $R_{20}$, together with the N atom to which they are bonded, are a 5-membered or 6-membered heterocyclic ring, $R_{21}$ is hydrogen, $C_1$–$C_{12}$-alkyl, $C_2$–$C_6$-alkenyl, chloromethyl, $C_5$–$C_8$-cycloalkyl, $C_7$–$C_{14}$-aralkyl, phenyl or $C_7$–$C_{10}$-alkylphenyl, or phenyl, phenylmethyl or phenylethyl which is substituted by 1 or 2 $C_1$–$C_4$-alkyl groups and 1 hydroxyl group, $R_{22}$ is hydrogen, $C_1$–$C_4$-alkyl, $C_3$–$C_4$-alkoxyalkyl, phenyl or phenoxymethyl, $R_{23}$ is hydrogen, $C_1$–$C_{12}$-alkyl or a group —$COR_{21}$ or —$CON(R_{19})(R_{20})$ and $R_{24}$ is $C_1$–$C_{12}$-alkyl, phenyl or $C_7$–$C_{10}$-alkylphenyl, Y is —O— or —$N(R_{25})$—, in which $R_{25}$ is hydrogen, $C_1$–$C_{18}$-alkyl, $C_3$–$C_{12}$-alkenyl, $C_3$–$C_{12}$-cycloalkyl, phenyl, $C_7$–$C_{14}$-aralkyl, $C_7$–$C_{14}$-alkaryl, $C_2$–$C_{11}$-alkoxyalkyl or a group of the formula IV, Z is —O— or —$N(R_{26})$—, in which $R_{26}$ is hydrogen, $C_1$–$C_{18}$-alkyl, $C_3$–$C_{12}$-alkenyl, $C_3$–$C_{12}$-cycloalkyl, phenyl, $C_7$–$C_{14}$-alkaryl, $C_7$–$C_{14}$-aralkyl, $C_2$–$C_{11}$-alkoxyalkyl or a group —$COR_{27}$, —$COOR_{28}$, —$CON(R_{29})(R_{30})$, —$CH_2$—$CH(R_{31})$—$OR_{32}$, —$SOR_{33}$ or —$SO_2R_{33}$, in which $R_{27}$ has one of the meanings given for $R_{21}$ or is a heterocyclic ring, $R_{28}$ has one of the meanings given for $R_{18}$, $R_{29}$ has one of the meanings given for $R_{19}$, $R_{30}$ has one of the meanings given for $R_{20}$, $R_{31}$ has one of the meanings given for $R_{22}$, $R_{32}$ has one of the meanings given for $R_{23}$ and $R_{33}$ has one of the meanings given for $R_{24}$, or $R_{26}$ is one of the groups

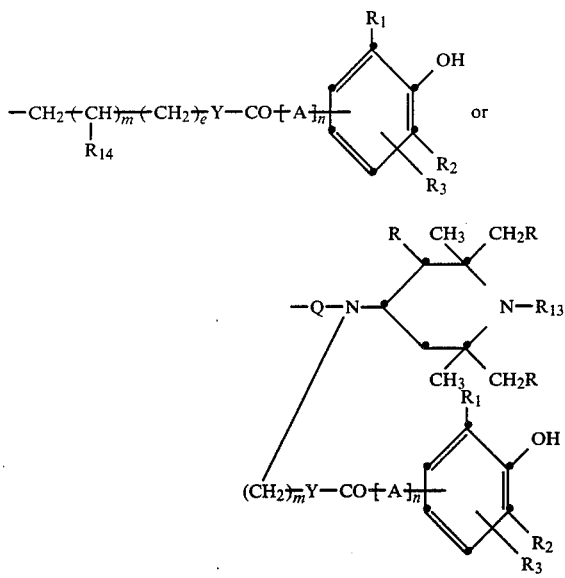

Q is a group $-(C_bH_{2b})-$, in which b is an integer of from 2 to 12, $C_4-C_8$-alkenylene, $C_5-C_{12}$-cycloalkylene, phenylene, xylylene bitolylene, a group $-CO-(C_rH_{2r})-CO-$,

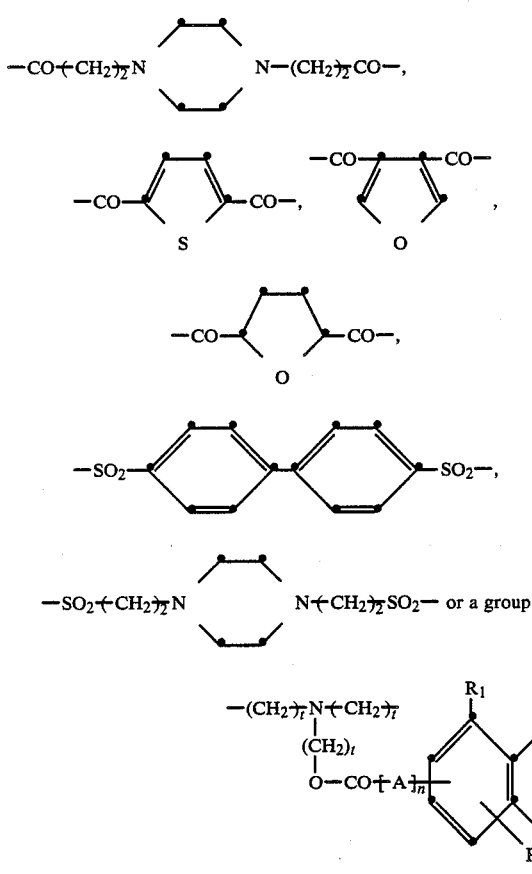

in which t is 0 or an integer of from 1 to 5, or $R_{13}$ is a group of the formula

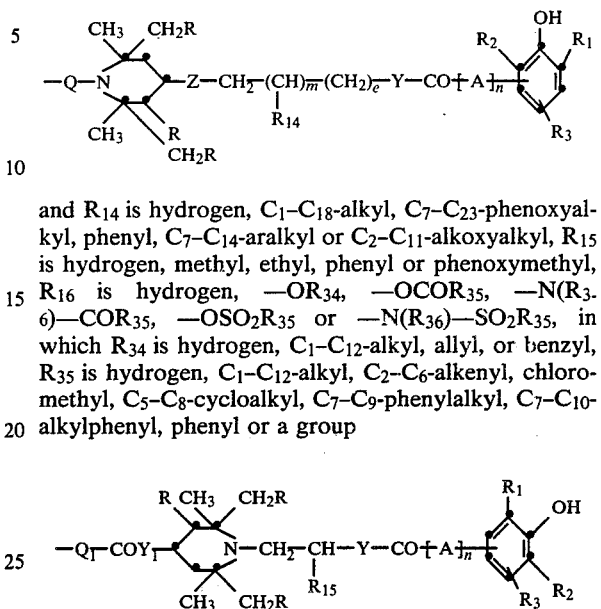

and $R_{14}$ is hydrogen, $C_1-C_{18}$-alkyl, $C_7-C_{23}$-phenoxyalkyl, phenyl, $C_7-C_{14}$-aralkyl or $C_2-C_{11}$-alkoxyalkyl, $R_{15}$ is hydrogen, methyl, ethyl, phenyl or phenoxymethyl, $R_{16}$ is hydrogen, $-OR_{34}$, $-OCOR_{35}$, $-N(R_{36})-COR_{35}$, $-OSO_2R_{35}$ or $-N(R_{36})-SO_2R_{35}$, in which $R_{34}$ is hydrogen, $C_1-C_{12}$-alkyl, allyl, or benzyl, $R_{35}$ is hydrogen, $C_1-C_{12}$-alkyl, $C_2-C_6$-alkenyl, chloromethyl, $C_5-C_8$-cycloalkyl, $C_7-C_9$-phenylalkyl, $C_7-C_{10}$-alkylphenyl, phenyl or a group

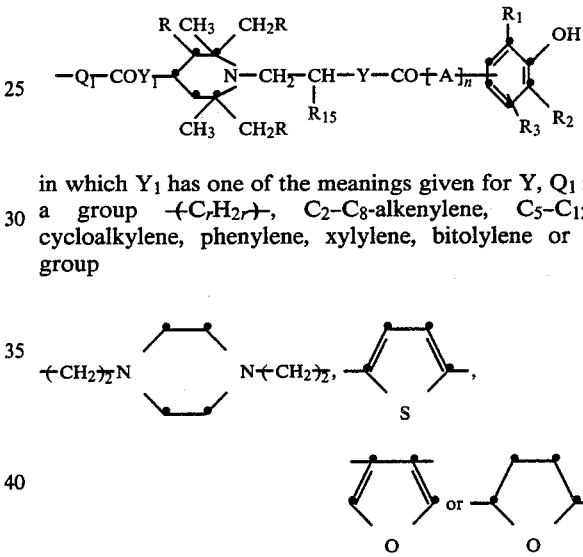

in which $Y_1$ has one of the meanings given for Y, $Q_1$ is a group $-(C_rH_{2r})-$, $C_2-C_8$-alkenylene, $C_5-C_{12}$-cycloalkylene, phenylene, xylylene, bitolylene or a group and $R_{36}$ is hydrogen, $C_1-C_{12}$-alkyl, $C_5-C_8$-cycloalkyl or benzyl, and $R_{17}$ is hydrogen, cyano, $-COOR_{18}$, $-CONH_2$, $-CON-(R_{19})(R_{20})$ or $-CH_2NHR_{37}$, in which $R_{37}$ is a group $-COR_{21}$ $-COOR_{18}$, $-CON(R_{19})(R_{20})$, $-CH_2-CH(R_{22})-OR_{23}$, $-SOR_{24}$ or $-SO_2R_{24}$, the radicals and symbols mentioned repeatedly always being as first defined.

2. A recording material for colour photography according to claim 1, which contains as the stabiliser at least one compound of the formula I, wherein Z is $-N(R')-$ and in which R' is a group $-COR_{27}$, $COOR_{28}$, $-CON(R_{29})(R_{30})$, $-SOR_{33}$ or $-SO_2R_{33}$ and the symbols $R_{27}$, $R_{28}$, $R_{29}$, $R_{30}$ and $R_{33}$ have one of the meanings given in claim 1.

3. A recording material for colour photography according to claim 2, which contains as the stabiliser at least one compound of the formula I, wherein $R_{13}$ is a group $-COR_{21}$, $-COOR_{18}$, $-CON(R_{19})(R_{20})$, $-SOR_{24}$ or $-SO_2R_{24}$ and the symbols $R_{21}$, $R_{18}$, $R_{19}$, $R_{20}$ and $R_{24}$ have one of the meanings given in claim 1.

4. A recording material for colour photography according to claim 1, which contains, as the stabiliser, at least one polyalkylpiperidine compound of the formula V

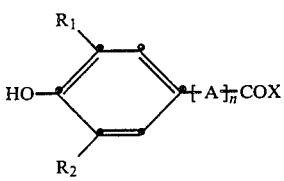
(V)

in which n is the number 0 or 1, $R_1$ is hydrogen or $C_1$-$C_4$-alkyl, $R_2$ is $C_1$-$C_4$-alkyl, A is a group —$CH_2$—, —$CH_2$—$CH(R_5)$,

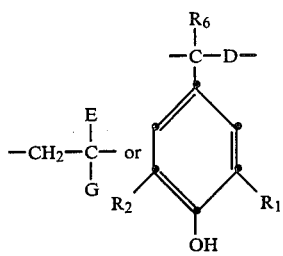

in which $R_5$ and $R_6$ are hydrogen or methyl, E is cyano, —$COCH_3$ or —$COOCH_3$, G is hydrogen, $C_1$-$C_{18}$-alkyl, allyl, cyclohexyl, benzyl or a group

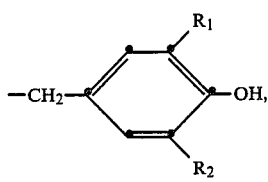

or E and G together are a group —CO—$(CH_2)_4$—, D is a group —$(C_rH_{2r})$—, in which r is a number from 0 to 6, and X is a group of the formula

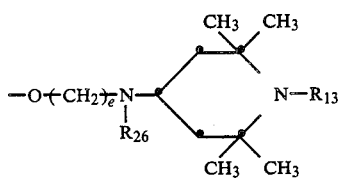

or of the formula

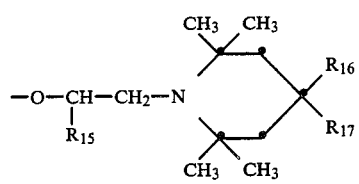

in which e is an integer of from 2 to 3, $R_{13}$ is hydroxyl, methyl, allyl, benzyl, 2-hydroxyethyl, acetyl, acroyl or a group of the formula —$CON(R_{19})(R_{20})$, in which $R_{19}$ is $C_1$-$C_8$-alkyl, cyclohexyl or phenyl and $R_{20}$ is hydrogen or $C_1$-$C_{12}$-alkyl, $R_{26}$ is hydrogen, $C_1$-$C_8$-alkyl or a group —$COR_{27}$, —$COOR_{28}$, —CON—$(R_{29})(R_{30})$, —$CH_2$—$CH(R_{31})$—$OR_{32}$ or —$SO_2R_{33}$, in which $R_{27}$ is $C_1$-$C_{12}$-alkyl, $C_2$-$C_4$-alkenyl, cyclohexyl, benzyl, phenyl, 2-(3,5-di-tert.-butyl-4-hydroxyphenyl)-ethyl or a heterocyclic ring, $R_{28}$ is $C_1$-$C_8$-alkyl, allyl or cyclohexyl, $R_{29}$ is $C_1$-$C_{12}$-alkyl, cyclohexyl or phenyl and $R_{30}$ is hydrogen or $C_1$-$C_{12}$-alkyl, or $R_{29}$ and $R_{30}$, together with the N atom to which they are bonded, are a 6-membered heterocyclic ring, $R_{31}$ is hydrogen, methyl or phenyl and $R_{32}$ is hydrogen, $C_1$-$C_4$-alkyl or a group —$COR_{21}$ or —$CON(R_{19})(R_{20})$ and $R_{33}$ is $C_1$-$C_{12}$-alkyl, phenyl or $C_7$-$C_{10}$-alkylphenyl, $R_{15}$ is hydrogen, methyl or phenyl, $R_{16}$ is hydrogen, —$OR_{34}$, —$OCOR_{35}$, or —$N(R_{36})$—$COR_{35}$, in which $R_{34}$ is hydrogen, $C_1$-$C_8$-alkyl, allyl, benzyl or phenyl, $R_{35}$ is hydrogen, $C_1$-$C_8$-alkyl, allyl benzyl or phenyl and $R_{36}$ is hydrogen, $C_1$-$C_4$-alkyl, cyclohexyl or benzyl, and $R_{17}$ is hydrogen, cyano, —$COOR_{18}$, —$CONH_2$, —$CO$-$N$—$(R_{19})(R_{20})$ or —$CH_2NHR_{37}$, in which $R_{37}$ is a group —$COR_{21}$, —$COOR_{18}$, —$CON(R_{19})(R_{20})$ or —$CH_2$—$CH(R_{22})$—$OR_{23}$, the radicals and symbols repeatedly mentioned in this claim always being as first defined in this claim.

5. A recording material for colour photography according to claim 4, which contains, as the stabiliser, at least one polyalkylpiperidine compound which is of the formula V in which n is the number 0 or 1, $R_1$ is hydrogen, methyl or tert.-butyl, $R_2$ is methyl or tert.-butyl, A is a group —$CH_2$— or —$CH_2CH_2$—, in which X is a group of the formula

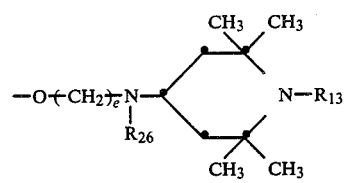

or of the formula

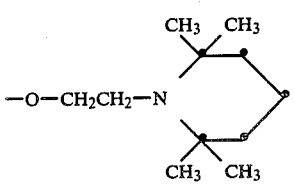

in which e is a number from 2 to 3, $R_{13}$ is methyl, allyl, benzyl, 2-hydroxyethyl, acetyl or acroyl and $R_{26}$ is hydrogen, $C_1$-$C_8$-alkyl or a group of the formula —$COR_{27}$ or —$SO_2R_{33}$, in which $R_{27}$ is $C_1$-$C_{12}$-alkyl or $C_2$-$C_4$-alkenyl and $R_{33}$ is $C_1$-$C_4$-alkyl, phenyl or p-tolyl.

6. A recording material for colour photography according to claim 1, which contains, as the stabiliser, at least one polyalkylpiperidine compound of the formula I in which A is one of the groups —$CH_2$—, —$CH_2$—$CH(R_5)$—,

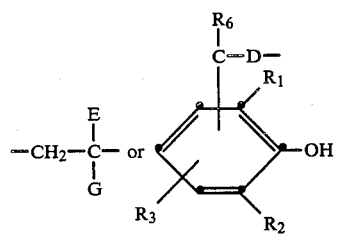

7. A recording material for colour photography according to claim 1, which contains, as the stabiliser, at least one polyalkylpiperidine compound which is of the formula VI

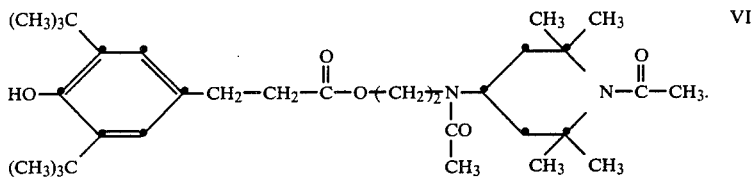

8. A recording material for colour photography according to claim 1, which contains, as the stabiliser, at least one polyalkylpiperidine compound which is of the formula VII

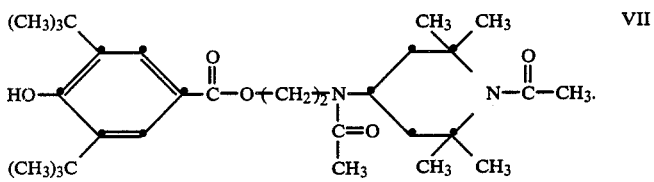

9. A recording material for colour photography according to claim 1, which contains, as the stabiliser, at least one polyalkylpiperidine compound which is of the formula VIII

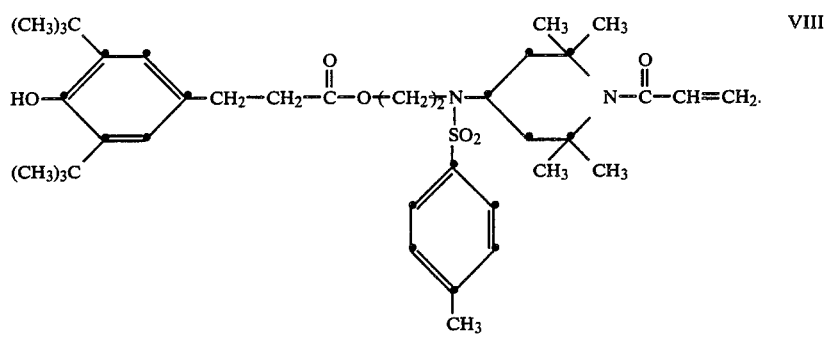

10. A recording material for colour photography according to claim 1, which contains, as the stabiliser, at least one polyalkylpiperidine compound which is of the formula IX

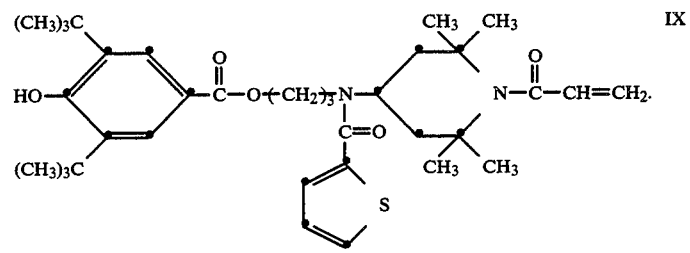

11. A recording material for colour photography according to claim 1, which contains, as the stabiliser, at least one polyalkylpiperidine compound which is of the formula X

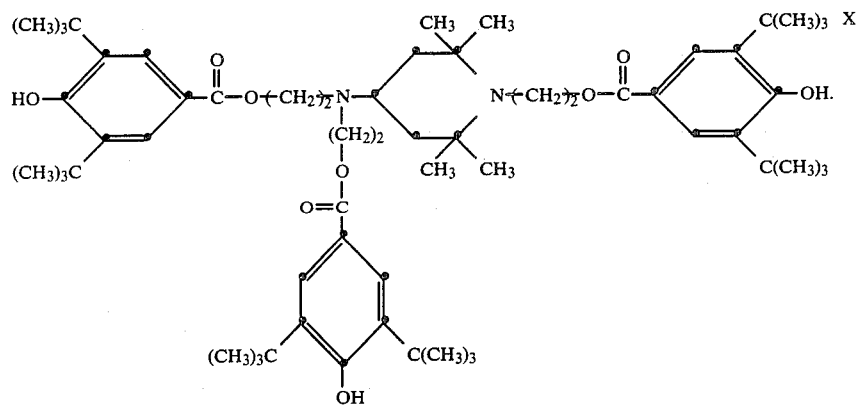

12. Recording material for colour photography according to claim 1, which contains a stabiliser of the formula I in combination with a blue-green, purple or yellow coupler.

13. Recording material for colour photography according to claim 1, which contains a stabiliser of the formula I in combination with ultraviolet absorbers.

14. Recording material for colour photography according to claim 13, wherein the ultraviolet absorbers are compounds of the benzophenone, acrylonitrile, thiazolidone, benzotriazole, oxazole, thiazole or imidazole type.

15. Recording material for colour photography according to claim 1, which contains a stabiliser of the formula I in combination with a blue-green, purple or yellow coupler and with a UV absorber in the same layer.

16. Recording material for colour photography according to claim 1, which contains 1 to 2,000 mg of the stabiliser of the formula I per $m^2$ of the layer in which it is incorporated.

17. Process for the preparation of photographic color-forming agents by imagewise exposure and color development of a recording material for color photography according to claim 1.

* * * * *

UNITED STATES PATENT AND TRADEMARK OFFICE
CERTIFICATE OF CORRECTION

PATENT NO.  : 4,629,682
DATED       : December 16, 1986
INVENTOR(S) : DAVID G. LEPPARD and JEAN RODY It is certified that error appears in the above-identified patent and that said Letters Patent is hereby corrected as shown below:

Title page, first column, in the line entitled

"[73] Assignee", change "Canada" to --Switzerland--.

Signed and Sealed this

Twenty-seventh Day of October, 1987

Attest:

DONALD J. QUIGG

*Attesting Officer*　　　　*Commissioner of Patents and Trademarks*